United States Patent [19]

Wee

[11] Patent Number: 4,977,270
[45] Date of Patent: Dec. 11, 1990

[54] SUBSTITUTED 2,4-DIOXODIAZOLIDINES AND -THIADIAZOLIDINES AND THEIR USE AS HERBICIDES

[75] Inventor: Siok-Hui H. Wee, Berkeley, Calif.

[73] Assignee: ICI Americas Inc., Wilmington, Del.

[21] Appl. No.: 278,708

[22] Filed: Dec. 1, 1988

[51] Int. Cl.$^5$ .................... C07D 233/02; A01N 43/50
[52] U.S. Cl. .......................... 548/314; 71/92
[58] Field of Search ............................ 548/314; 71/92

[56] References Cited

U.S. PATENT DOCUMENTS 3,134,663  5/1964  Kroll ............................... 548/314 X
3,846,441  11/1974  Mine et al. ........................... 548/314

FOREIGN PATENT DOCUMENTS 56-150070  11/1988  Japan .

Primary Examiner—Alan L. Rotman
Assistant Examiner—Joseph K. McKane
Attorney, Agent, or Firm—Denis A. Polyn

[57] ABSTRACT

Specific substituted 2,4-dioxodiazolidines and 2,4-dioxothiadiazolidines falling within the general formula

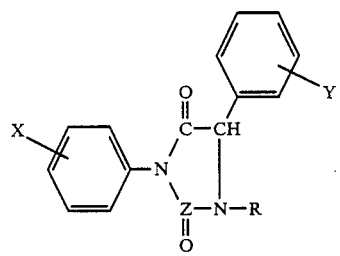

in which R is lower alkyl; X is H, halo, lower alkyl, trifluoromethyl, or lower alkoxy, including multiple substituents; Y is H, halo, lower alkyl, trifluoromethyl, lower alkoxy, or phenoxy, including multiple substituents; and Z is C or S; are useful as herbicidal agents.

18 Claims, No Drawings

SUBSTITUTED 2,4-DIOXODIAZOLIDINES AND -THIADIAZOLIDINES AND THEIR USE AS HERBICIDES

BACKGROUND AND SUMMARY OF THE INVENTION

This invention relates to certain substituted 2,4-dioxodiazolidines and 2,4-dioxothiadiazolidines and to their use in herbicidal formulations. In particular, this invention relates to certain specific compounds falling within the general formula

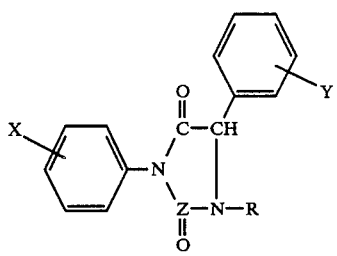

in which R is lower alkyl; X is H, halo, lower alkyl, trifluoromethyl, or lower alkoxy, including multiple substituents; Y is H, halo, lower alkyl, trifluoromethyl, lower alkoxy, or phenoxy, including multiple substituents; and Z is C or S.

The compounds of the present invention, as will be seen from the description and test data which follow, have utility as both pre-emergence and post-emergence herbicides against a wide range of plant species. These compounds are of particular utility in the control of weeds associated with corn crops. undesired plant growth. Inhibitive control and modification include all deviations from natural development such as, for example, total killing, growth retardation, defoliation, desiccation, regulation, stunting, tillering, stimulation, leaf burn, and dwarfing. The term "herbicidally effective amount" is used to denote any amount which achieves such control or modification when applied to the undesired plants themselves or to the area in which these plants are growing. The term "plants" is intended to include germinant seeds, emerging seedlings and established vegetation, including both roots and aboveground portions.

DETAILED DESCRIPTION OF THE INVENTION AND PREFERRED EMBODIMENTS

The specific compounds of the present invention are as follows:

I. Compounds having the formula

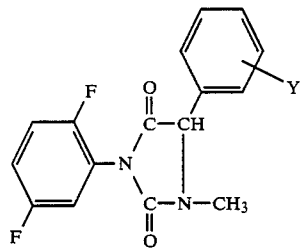

in which Y is H, 2-F, 4-F, 3-Cl, 4-Cl, 2,4-di-Cl, 3,4-di-Cl, 2-Br, 3-Br, 4-Br, 4-I, 4-CH$_3$, 4-t-C$_4$H$_9$, 3-OCH$_3$, 4-OC$_2$H$_5$ or 3-OC$_6$H$_5$;

II. Compounds having the formula

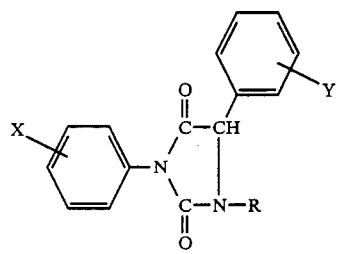

in which X is 2-F, 3-Cl, 2,5-di-F-4-CH$_3$ or 2-F-5-OCH$_3$;

III. Compounds having the formula

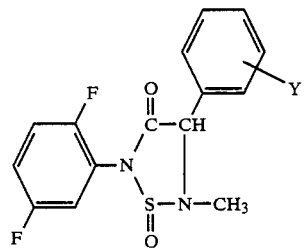

in which the combination of X, Y and R is either
(a) X=2,5-di-F, Y=H, and R=C$_2$H$_5$;
(b) X=2,5-di-F, Y=4-Br, and R=C$_2$H$_5$;
(c) X=3-CF$_3$, Y=H, and R=C$_2$H$_5$;
(d) X=3,4-di-Cl, Y=H, and R=C$_2$H$_5$; or
(e) X=2,5-di-F, Y=H, and R=n-C$_4$H$_9$.

IV. Compounds having the formula in which Y is H, 4-F, 3-Cl, 4-Cl, or 4-CH$_3$.

Within the scopes of these formulas, certain embodiments are preferred, as follows.

In formula I, Y is preferably H, 2-F, 4-F, 3-Cl, 4-Cl, 3,4-di-Cl, 3-Br, 4-Br, 4-I, 4-CH$_3$, or 3-OCH$_3$.

In formula II, X is preferably 2-F or 3-Cl.

In formula III, the preferred combinations are X=2,5-di-F, Y=H, and R=C$_2$H$_5$; and X=2,5-di-F, Y=4-Br, and R=C$_2$H$_5$.

In formula IV, Y is preferably H, 3-Cl, or 4-F.

It will be noted that these formulas indicate a chiral center at the 5-position of the heterocyclic ring. The various compounds listed herein each represent a mixture of enantiomers at this position. Herbicidal activity for the mixture is an indication of herbicidal activity for each individual enantiomer. It is to be expected however that in certain cases one enantiomer will have greater herbicidal activity than the other.

The compounds of this invention may be prepared as follows. An N-phenyl-2-chloro-2-phenyl acetamide with appropriate substituents on the phenyl rings for X and Y is first prepared. For compounds where Y is H, this intermediate may be prepared by reacting X-substituted anilines with 2-chloro-2-phenylacetyl chloride in dichloromethane or toluene with an acid scavenger at room temperature. For compounds where Y is other than H, this intermediate is prepared by first preparing the N-(X-phenyl)-2,2-dichloro-3-(Y-phenyl)aziridine by the addition of dichlorocarbene to the imine made from the X-substituted aniline and the Y-substituted benzaldehyde, and then hydrolyzing the N-(X-phenyl)-2,2-dichloro-3-(Y-phenyl)aziridine.

The N-phenyl-2-chloro-2-phenyl acetamide (bearing the appropriate substituents) may then be converted to the N-phenyl-2-alkylamino-2-phenyl acetamide by reaction with primary alkylamines in an alcohol solvent at ambient temperature with a catalytic amount of potassium iodide. To form final products where Z is a carbon atom, the N-phenyl-2-alkylamino-2-phenyl acetamide is reacted with 1,1'-carbonyldiimidazole in benzene under reflux conditions. Final products where Z is a sulfur atom may be formed by reacting the N-phenyl-2-alkylamino-2-phenyl acetamide with thionyl chloride in the presence of an acid scavenger such as pyridine in dichloromethane at room temperature.

The following are examples of compounds which have been synthesized by the procedures described above. These examples are offered strictly for purposes of illustration, and are intended neither to limit nor to define the invention in any manner.

EXAMPLE 1

This example demonstrates the preparation of 3-(2,5-difluorophenyl)-5-(4-bromophenyl)-1-methylimidazolidine-2,4-dione, in which X is 2,5-difluoro, Y is 4-bromo, Z is C, and R is methyl, according to the general formula shown above. This compound is represented in Table I-A below as Compound No. 4.

The synthesis was begun by the preparation of N-(2,5-difluorophenyl)-4-bromobenzylidene amine as follows. A mixture of 2,5-difluoroaniline (15.0 g, 0.12 mol) and 4-bromobenzaldehyde (21.5 g, 0.12 mol) in toluene (100 mL) was heated overnight under a Dean Stark trap. The reaction was cooled to room temperature and the solvent was removed in a rotary evaporator. A crude product of 45.6 g (exceeding theoretical yield) was obtained, in the form of a solid having a melting point range of 68°–70° C.

This was then converted to N-(2,5-difluorophenyl)-2,2-dichloro-3-(4-bromophenyl) aziridine as follows. To a methylene chloride solution of the N-(2,5-difluorophenyl)-4-bromobenzylidene amine was added chloroform (25 mL, 0.31 mol) and tetrabutylphosphonium bromide (1.7 g, catalytic). While mixing with a mechanical stirrer, a 50% (weight/volume) aqueous solution of sodium hydroxide (62 mL, 0.78 mol) was added to the reaction mixture through an addition funnel. The mixture turned dark brown with a slight exotherm and was allowed to stir overnight at room temperature. The resulting mixture was poured into a separatory funnel and more methylene chloride (100 mL) was added. The lower layer (sodium hydroxide solution) was then drained off. The methylene chloride phase was then washed twice with 50-mL portions of water, dried with MgSO$_4$, filtered, and concentrated in a rotary evaporator to give a crude liquid (45 g, 103% yield).

The aziridine was then converted to N-(2,5-difluorophenyl)-2-chloro-2-(4-bromophenyl) acetamide as follows. The crude aziridine (44.0 g, 0.12 mol) was combined with water (200 mL) and the resulting mixture was heated under reflux until gas chromatography indicated no further reaction. The mixture was then cooled to room temperature. The product was extracted with ethyl acetate (200 mL), dried with MgSO$_4$, filtered, and concentrated in a rotary evaporator to give 99.9 g (95% crude yield) of a brown solid.

The latter was then converted to N-(2,5-difluorophenyl)-2-methylamino-2-(4-bromophenyl)acetamide as follows. An ethanolic solution (25 mL) of N-(2,5-difluorophenyl)-2-chloro-2-(4-bromophenyl)acetamide (7.0 g, 0.02 mol) was combined with 40% aqueous ethylamine (25 mL, 0.25 mol) and potassium iodide (about 0.5 g, catalytic), and the resulting mixture was stirred at room temperature for three days. The ethanol was then removed in a rotary evaporator. The residue was dissolved in ethyl acetate (75 mL) and washed with two 25-mL portions of water, dried over magnesium sulfate and filtered. The solvent was then removed and the product isolated and purified through a short column of silica gel using 5% ethyl acetate in hexanes as eluent. The result was a thick oil (4.6 g, 35% yield).

This was then converted to the final product as follows. A benzene solution of the N-(2,5-difluorophenyl)-2-methylamino-2-(4-bromophenyl)acetamide (2.0 g, 6 mmol) was combined with 1,1'-carbonyldiimidazole (1.0 g, 6.2 mmol) and the resulting mixture heated under reflux for thirty minutes. The mixture was stirred at room temperature for three days, diluted with ethyl ether (20 mL), washed with water (50 mL), dried with MgSO$_4$, filtered and concentrated in a rotary evaporator to give 1.4 g (67% yield) of the desired product in the form of a thick oil. The structure was confirmed as that of 3-(2,5-difluorophenyl)-5-(4-bromophenyl)-1-methylimidazolidine-2,4-dione by nuclear magnetic resonance (NMR), mass spectroscopy (MS) and infrared spectrophotometry (IR).

EXAMPLE 2

This example demonstrates the preparation of 2-(2,5-difluorophenyl)-5-methyl-1-oxo-4-phenyl-1,2,5-thiadiazolidin-3-one, in which X is 2,5-difluoro, Y is H, Z is S, and R is methyl, according to the general formula shown above. This compound is represented in Table I-A below as Compound No. 25.

The synthesis began with the preparation of N-(2,5-difluorophenyl)-2-chloro-2-phenylacetamide as follows. A toluene (150 mL) solution of 2,5-difluoroaniline (25.0 g, 0.19 mol) and pyridine (16.8 g, 0.21 mol) was prepared and placed in an ice bath. To the solution was added 2-chloro-2-phenylacetyl chloride (40.2 g, 0.21 mol) through an addition funnel. The mixture was stirred at room temperature overnight. Ethyl acetate (100 mL) and water (100 mL) were then added and the mixture transferred to a separatory funnel. The organic layer was collected, dried with MgSO$_4$, filtered, and concentrated in a rotary evaporator to give 57.4 g of crude material (105% yield).

The latter was converted to N-(2,5-difluorophenyl)-2-methylamino-2-phenylacetamide as follows. An ethanolic (300 mL) solution of the N-(2,5-difluorophenyl)-2-chloro-2-phenylacetamide (15 g, 0.05 mol) was combined with 40% aqueous methylamine (62 mL, 0.80 mol) and potassium iodide (2 g, catalytic amount). The mixture was stirred for four days, at which time completion of the reaction was confirmed by thin layer chromatography. The ethanol was removed in a rotary evaporator, and the residue was dissolved in ethyl acetate (200 mL) and washed with two 100-mL portions of water, dried over MgSO₄, and filtered. The product was isolated after the solvent was removed and the crude material was triturated with hexane to give 9.8 g (67% yield) of solid.

The final product was then prepared as follows. To a methylene chloride (50 mL) solution of the N-(2,5-difluorophenyl)-2-methylamino-2-phenylacetamide (1.5 g, 5.8 mmol) was added pyridine (1.4 g, 17 mmol) and thionyl chloride (1.04 g, 8.7 mmol) and the resulting mixture was stirred at room temperature overnight. The mixture was washed with water (20 mL), dried with MgSO₄, filtered, and concentrated in a rotary evaporator to give a solid (0.9 g, 47% yield) of melting point 105°–110° C. The structure of the product was confirmed as that of 2-(2,5-difluorophenyl)-5-methyl-1-oxo-4-phenyl-1,2,5-thiadiazolidin-3-one by nuclear magnetic resonance (NMR), mass spectroscopy (MS) and infrared spectrophotometry (IR).

These and further compounds prepared by similar procedures are listed in Tables I-A, I-B, I-C, I-D, II-A and II-B below, together with physical data in the form of melting point ranges where such measurements were possible, and physical descriptions where neither melting points nor refractive indices could be taken. The compounds listed in Tables I-A through I-D are within the scope of the invention, whereas those in Tables II-A and II-B are not.

TABLE I-A
COMPOUNDS WITHIN THE INVENTION

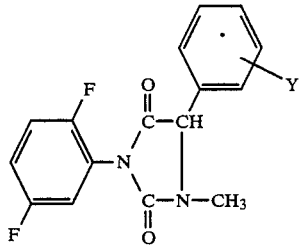

| Compound No. | Y | melting range (°C.) or description |
|---|---|---|
| 1 | H | 125.0–130.0 |
| 2 | 4-CH₃ | oil |
| 3 | 4-Cl | thick oil |
| 4 | 4-Br | thick oil |
| 5 | 4-t-C₄H₉ | 111.0–114.0 |
| 6 | 2,4-di-Cl | oil |
| 7 | 2-Br | 105.0–110.0 |
| 8 | 2-F | 91.0–95.0 |
| 9 | 4-I | oil |
| 10 | 3-OC₆H₅ | oil |
| 11 | 4-F | 143.0–146.0 |
| 12 | 3,4-di-Cl | 124.0–130.0 |
| 13 | 3-Br | oil |
| 14 | 3-OCH₃ | semi-solid |
| 15 | 4-OC₂H₅ | 50.0–55.0 |
| 16 | 3-Cl | semi-solid |

TABLE I-B
COMPOUNDS WITHIN THE INVENTION

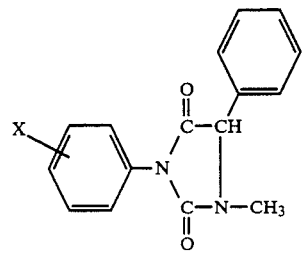

| Compound No. | X | melting range (°C.) or description |
|---|---|---|
| 17 | 2-F | thick oil |
| 18 | 2,5-di-F-4-CH₃ | oil |
| 19 | 3-Cl | 177.0–180.0 |
| 20 | 2-F-5-OCH₃ | 122.0–128.0 |

TABLE I-C
COMPOUNDS WITHIN THE INVENTION

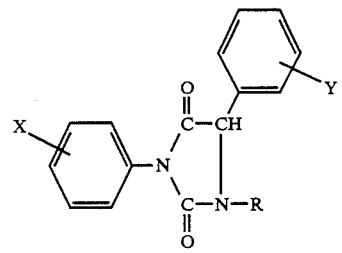

| Compound No. | X | Y | R | melting range (°C.) or description |
|---|---|---|---|---|
| 21 | 2,5-di-F | H | C₂H₅ | 100.0–109.0 |
| 22 | 2,5-di-F | 4-Br | C₂H₅ | thick oil |
| 23 | 3-CF₃ | H | C₂H₅ | 106.0–108.0 |
| 24 | 3,4-di-Cl | H | C₂H₅ | 112.0–120.0 |
| 25 | 2,5-di-F | H | n-C₄H₉ | yellow oil |

TABLE I-D
COMPOUNDS WITHIN THE INVENTION

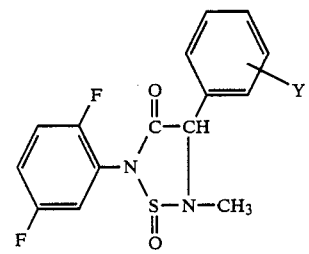

| Compound No. | Y | melting range (°C.) or description |
|---|---|---|
| 26 | H | 105.0–110.0 |
| 27 | 4-CH₃ | 74.0–80.0 |
| 28 | 4-Cl | oil |
| 29 | 4-F | 83.0–86.0 |
| 30 | 3-Cl | oil |

TABLE II-A
COMPOUNDS OUTSIDE THE INVENTION

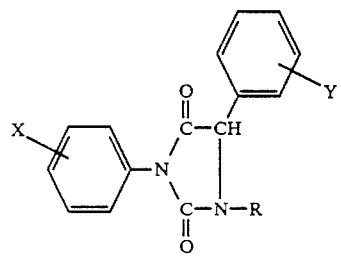

| Compound No. | X | Y | R | melting range (°C.) or description |
|---|---|---|---|---|
| 101 | 3-CF$_3$ | H | CH$_3$ | 151.0–154.0 |
| 102 | 3,4-di-Cl | H | CH$_3$ | 184.0–187.0 |
| 103 | 2-Cl | H | CH$_3$ | oil |
| 104 | 3-Cl-4-F | H | CH$_3$ | 164.0–169.0 |
| 105 | penta-F | H | CH$_3$ | 135.0–138.0 |
| 106 | 2-F-4-Cl-5-O-i-C$_3$H$_7$ | H | CH$_3$ | 107.0–110.0 |
| 107 | 2,5-di-F-4-CH$_3$ | 4-Cl | CH$_3$ | 135.0–140.0 |
| 108 | 2,5-di-F-4-CH$_3$ | 4-CH$_3$ | CH$_3$ | oil |

TABLE II-B
COMPOUNDS OUTSIDE THE INVENTION

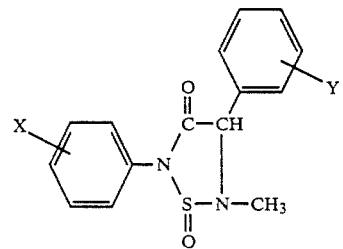

| Compound No. | X | Y | R | melting range (°C.) or description |
|---|---|---|---|---|
| 109 | 3-CF$_3$ | H | C$_2$H$_5$ | oil |
| 110 | 2,5-di-F | 4-t-C$_4$H$_9$ | CH$_3$ | 112.0–122.0 |
| 111 | 2,5-di-F | 2-Br | CH$_3$ | 105.0–110.0 |
| 112 | 2,5-di-F | 3-OC$_6$H$_5$ | CH$_3$ | oil |
| 113 | 2-F | 3-CF$_3$ | C$_2$H$_5$ | oil |
| 114 | 2,5-di-F | 3-OCH$_3$ | CH$_3$ | semi-solid |

The compounds listed in the foregoing tables were tested for herbicidal activity by various methods and at various rates of application. The results of some of these tests are given below. As one skilled in the art is aware, the results obtained in herbicidal screening tests are affected by a number of factors that are not readily controllable. Environmental conditions such as amount of sunlight and water, soil type, soil pH, temperature and humidity, are examples of such factors. The depth of planting and the application rate of the herbicide, as well as the nature of crops being tested, can also affect the test results. Results will also vary from crop to crop and within the crop varieties.

The test procedures used are as follows:

Pre-Emergence Herbicidal Evaluation

Planting flats were filled with sandy loam soil containing a fungicide and fertilizer. The soil was leveled and rows of grassy weeds, broadleaf weeds and yellow nutsedge (*Cyperus esculentus*), were planted thickly enough so that several seedlings emerged per inch of row. The grassy weeds were green foxtail (*Setaria viridis*), watergrass (*Echinochloa crusgalli*) and wild oat (*Avena fatua*). Broadleaf weeds utilized were annual morningglory (*Ipomoea purpurea*), velvetleaf (*Abutilon theophrasti*), and wild mustard (*Brassica kaber*).

Solutions of the test compounds were made by weighing out 333 mg of the test compound into a 60-mL wide-mouth bottle, then dissolving the compound in 25 mL of acetone containing 1% Tween ® 20 (polyoxyethylene sorbitan monolaurate emulsifier). Additional solvents, not exceeding 5 mL, were used if needed to dissolve the compound. A 20.5-mL aliquot was then taken from the solution and diluted with 25 mL of an acetone:water mixture (19:1) containing 1% Tween ® 20. This was used as the spray solution.

One day after planting, the flats were sprayed with the spray solution at a rate of 80 gallons of solution per acre with the compound being applied at a rate of 4 pounds per acre (4.48 kg/ha).

The flats were then returned to the greenhouse and watered daily by sprinkling. The degree of weed control was estimated and recorded 3 weeks after treatment, as percentage control compared to the growth of the same species in an untreated check flat of the same age.

The percent control is the total injury to the plants due to all factors, including inhibited germination, killing of the plant tissue after emergence, stunting, malformation, chlorosis, and other types of injury. The control ratings vary from 0 to 100 percent, where 0 represents no effect with growth equal to the untreated control, and 100 represents complete kill; a dash indicates that no test was performed at that level of application.

Post-Emergence Herbicidal Evaluation

The soil was prepared and seeded with the same varieties used in the pre-emergence test. The flats were placed in the greenhouse at 70°–85° F. (21°–29° C.) and watered by sprinkling. Twelve to fourteen days after planting, the flats were sprayed at a rate of 80 gallons of solution per acre. Each compound was applied at the rate of 4 pounds/acre (4.48 kg/ha), using a spray solution prepared as in the pre-emergence test.

The flats were returned to the greenhouse after spraying and watered daily without wetting the foliage. Three weeks after treatment the degree of weed control was estimated and recorded as percentage control compared to the growth of the same species in an untreated check flat of the same age. The percent control ratings were assigned on the same basis as for the pre-emergence evaluation.

The following table lists the results of these tests, in terms of averages for the grasses and broadleaf weeds, with yellow nutsedge listed separately, in both pre- and post-emergence evaluations.

TABLE III
HERBICIDE TEST RESULTS
PERCENT CONTROL AT 4 LB/ACRE

| Compound No. | Pre-Emergence | | | Post-Emergence | | |
|---|---|---|---|---|---|---|
| | YNS | AVG | AVB | YNS | AVG | AVB |
| 1 | 0 | 100 | 100 | 0 | 100 | 100 |
| 2 | 10 | 100 | 100 | 20 | 100 | 100 |
| 3 | 0 | 100 | 100 | 20 | 100 | 100 |
| 4 | 0 | 100 | 100 | 80 | 100 | 100 |
| 5 | 0 | 100 | 100 | 0 | 40 | 100 |
| 6 | 0 | 100 | 100 | 0 | 0 | 0 |
| 7 | 0 | 75 | 100 | 0 | 0 | 0 |

TABLE III-continued
HERBICIDE TEST RESULTS
PERCENT CONTROL AT 4 LB/ACRE

| Compound No. | Pre-Emergence | | | Post-Emergence | | |
|---|---|---|---|---|---|---|
| | YNS | AVG | AVB | YNS | AVG | AVB |
| 8 | 10 | 100 | 100 | 10 | 100 | 100 |
| 9 | 0 | 100 | 100 | 80 | 100 | 100 |
| 10 | 0 | 10 | 17 | 0 | 0 | 0 |
| 11 | 0 | 100 | 100 | 0 | 93 | 100 |
| 12 | 0 | 100 | 100 | 10 | 87 | 100 |
| 13 | 0 | 100 | 100 | 0 | 97 | 100 |
| 14 | 0 | 100 | 100 | 0 | 67 | 100 |
| 15 | 0 | 88 | 87 | 0 | 0 | 100 |
| 16 | 0 | 100 | 100 | 30 | 100 | 100 |
| 17 | 0 | 100 | 100 | 0 | 95 | 100 |
| 18 | 0 | 100 | 97 | 0 | 0 | 63 |
| 19 | 0 | 0 | 13 | 0 | 0 | 0 |
| 20 | 0 | 33 | 0 | 0 | 0 | 0 |
| 21 | 0 | 98 | 73 | 0 | 10 | 77 |
| 22 | 0 | 92 | 73 | 0 | 83 | 100 |
| 23 | 0 | 33 | 17 | 0 | 0 | 13 |
| 24 | 0 | 0 | 23 | 0 | 30 | 60 |
| 25 | 0 | 17 | 58 | 0 | 0 | 0 |
| 26 | 0 | 100 | 100 | 0 | 0 | 0 |
| 27 | 0 | 50 | 83 | 0 | 0 | 0 |
| 28 | 0 | 73 | 100 | 0 | 0 | 0 |
| 29 | 0 | 97 | 100 | 0 | 0 | 0 |
| 30 | 0 | 100 | 100 | 0 | 0 | 0 |
| 101 | 0 | 0 | 0 | 0 | 0 | 0 |
| 102 | 0 | 0 | 0 | 0 | 0 | 0 |
| 103 | 0 | 0 | 0 | 0 | 0 | 0 |
| 104 | 0 | 0 | 0 | 0 | 0 | 0 |
| 105 | 0 | 0 | 0 | 0 | 0 | 0 |
| 106 | 0 | 0 | 0 | 0 | 0 | 0 |
| 107 | 0 | 0 | 0 | 0 | 0 | 0 |
| 108 | 0 | 0 | 0 | 0 | 0 | 0 |
| 109 | 0 | 0 | 0 | 0 | 0 | 0 |
| 110 | 0 | 0 | 0 | 0 | 0 | 0 |
| 111 | 0 | 0 | 0 | 0 | 0 | 0 |
| 112 | 0 | 0 | 0 | 0 | 0 | 0 |
| 113 | 0 | 0 | 0 | 0 | 0 | 0 |
| 114 | 0 | 0 | 0 | 0 | 0 | 0 |

Abbreviations:
YNS: Yellow Nutsedge
AVG: Grasses averaged
AVB: Broadleaf weeds averaged The compounds of the present invention are useful as herbicides and can be applied in a variety of ways known to those skilled in the art, at various concentrations. In practice, the compounds are applied as formulations containing the various adjuvants and carriers known to or used in the industry for facilitating dispersion. The choice of formulation and mode of application for any given compound may affect its activity, and selection will be made accordingly. The compounds of the invention may thus be formulated as granules, as wettable powders, as emulsifiable concentrates, as powders or dusts, as flowables, as solutions, suspensions or emulsions, or in controlled-release forms such as microcapsules. These formulations may contain as little as about 0.5% to as much as about 95% or more by weight of active ingredient. The optimum amount for any given compound will depend upon the nature of the seeds or plants to be controlled. The rate of application will generally vary from about 0.01 to about 10 pounds per acre, preferably from about 0.02 to about 4 pounds per acre.

Wettable powders are finely divided particles which disperse readily in water or other liquid carriers. The particles contain the active ingredient retained in a solid matrix. Typical solid matrices include fuller's earth, kaolin clays, silicas and other readily wet organic or inorganic solids. Wettable powders normally contain about 5% to about 95% of the active ingredient plus a small amount of wetting, dispersing, or emulsifying agent.

Emulsifiable concentrates are homogeneous liquid compositions dispersible in water or other liquid, and may consist entirely of the active compound with a liquid or solid emulsifying agent, or may also contain a liquid carrier, such as xylene, heavy aromatic naphthas, isophorone and other non-volatile organic solvents. In use, these concentrates are dispersed in water or other liquid and normally applied as a spray to the area to be treated. The amount of active ingredient may range from about 0.5% to about 95% of the concentrate.

Granular formulations include both extrudates and relatively coarse particles, and are usually applied without dilution to the area in which suppression of vegetation is desired. Typical carriers for granular formulations include sand, fuller's earth, attapulgite clay, bentonite clays, montmorillonite clay, vermiculite, perlite and other organic or inorganic materials which absorb or which can be coated with the active compound. Granular formulations normally contain about 5% to about 25% active ingredients which may include surface-active agents such as heavy aromatic naphthas, kerosene or other petroleum fractions, or vegetable oils; and/or stickers such as dextrins, glue or synthetic resins.

Dusts are free-flowing admixtures of the active ingredient with finely divided solids such as talc, clays, flours and other organic and inorganic solids which act as dispersants and carriers.

Microcapsules are typically droplets or granules of the active material enclosed in an inert porous shell which allows escape of the enclosed material to the surroundings at controlled rates. Encapsulated droplets are typically about 1 to 50 microns in diameter. The enclosed liquid typically constitutes about 50 to 95% of the weight of the capsule, and may include solvent in addition to the active compound. Encapsulated granules are generally porous granules with porous membranes sealing the granule pore openings, retaining the active species in liquid form inside the granule pores. Granules typically range from 1 millimeter to 1 centimeter, preferably 1 to 2 millimeters in diameter. Granules are formed by extrusion, agglomeration or prilling, or are naturally occurring. Examples of such materials are vermiculite, sintered clay, kaolin, attapulgite clay, sawdust and granular carbon. Shell or membrane materials include natural and synthetic rubbers, cellulosic materials, styrene-butadiene copolymers, polyacrylonitriles, polyacrylates, polyesters, polyamides, polyureas, polyurethanes and starch xanthates.

Other useful formulations for herbicidal applications include simple solutions of the active ingredient in a solvent in which it is completely soluble at the desired concentration, such as acetone, alkylated napthalenes, xylene and other organic solvents. Pressurized sprays, wherein the active ingredient is dispersed in finely-divided form as a result of vaporization of a low boiling dispersant solvent carrier, such as the Freons, may also be used.

Many of these formulations include wetting, dispersing or emulsifying agents. Examples are alkyl and alkylaryl sulfonates and sulfates and their salts; polyhydric alcohols; polyethoxylated alcohols; esters and fatty amines. These agents when used normally comprise from 0.1% to 15% by weight of the formulation.

The compounds of the present invention are also useful when combined with other herbicides and/or defoliants, desiccants, growth inhibitors, and the like. These other materials can comprise from about 5% to about 95% of the active ingredients in the formulations. These combinations frequently provide a higher level of effectiveness in controlling weeds and often provide results unattainable with separate formulations of the individual herbicides.

Examples of other herbicides, defoliants, desiccants and plant growth inhibitors with which the compounds of this invention can be combined are:

chlorophenoxy herbicides such as 2,4-D, 2,4,5-T, MCPA, MCPB, 2,4-DB, 2,4-DEB, 4-CPA, 2,4,5-TB, and silvex;

carbamate herbicides such as propham, chlorpropham, swep, and barban;

thiocarbamate and dithiocarbamate herbicides such as CDEC, metham-sodium, EPTC, diallate, PEBC, and vernolate;

substituted urea herbicides such as norea, dichloral urea, chloroxuron, cycluron, fenuron, monuron, monuron TCA, diuron, linuron, monolinuron neburon, buturon and trimeturon;

symmetrical triazine herbicides such as simazine, chlorazine, desmetryne, norazine, ipazine, prometryn, atrazine, trietazine, simetone, prometone, propazine and ametryne;

chlorinated aliphatic acid herbicides such as TCA and dalapon;

chlorinated benzoic acid and phenylacetic acid herbicides such as 2,3,6-TBA, dicamba, tricamba, chloramben, fenac, PBA, 2-methoxy-3,6-dichlorophenylacetic acid, 3-methoxy-2,6-dichlorophenylacetic acid, 2-methoxy-3,5,6trichlorophenylacetic acid and 2,4-dichloro-3-nitrobenzoic acid;

and such compounds as aminotriazole, maleic hydrazide, phenylmercury acetate, endothal, technical chlordane, DCPA, diquat, erbon, DNC, DNBP, dichlobenil, DPA, diphenamide, dipropalin, trifluralin, solan, dicryl, merphos, DMPA, DSMA, MSMA, potassium azide, acrolein, benefin, bensulide, AMS, bromacil, 2-(3,4-dichlorophenyl)-4-methyl-1,2,4-oxazolidine-3,5-dione, bromoxynil, cacodylic acid, CMA, CPMF, cypromid, DCB, DCPA, dichlone, diphenatril, DMTT, DNAP, EBEP, EXD, HCA, ioxynil, IPX, isocil, potassium cyanate, MAA, MAMA, MCPES, MCPP, MH, molinate, NPA, OCH, paraquat, PCP, picloram, DPA, PCA, sesone, terbacil, terbutol, TCBA, alachlor, nitralin, sodium tetraborate, calcium cyanamide, S,S,S-tributylphosphorotrithioate and propanil.

These formulations can be applied to the areas where control is desired by conventional methods. Dust and liquid compositions, for example, can be applied by the use of power-dusters, boom and hand sprayers and spray dusters. The formulations can also be applied from airplanes as a dust or a spray or by rope wick applications. To modify or control growth of germinating seeds or emerging seedlings, dust and liquid formulations can be distributed in the soil to a depth of at least one-half inch below the soil surface or applied to the soil surface only, by spraying or sprinkling. The formulations can also be applied by addition to irrigation water. This permits penetration of the formulations into the soil together with the irrigation water. Dust compositions, granular compositions or liquid formulations applied to the surface of the soil can be distributed below the surface of the soil by conventional means such as discing, dragging or mixing operations.

The following are examples of typical formulations.
5% dust:
 5 parts active compound
 95 parts talc
2% dust:
 2 parts active compound
 1 part highly dispersed silicic acid
 97 parts talc These dusts are formed by mixing the components then grinding the mixture to the desired particle size.

5% granules:
 5 parts active compound
 0.25 part epichlorohydrin
 0.25 part cetyl polyglycol ether
 3.5 parts polyethylene glycol
 91 parts kaolin (particle size 0.3-0.8 mm)

Granules are formed by mixing the active compound with epichlorohydrin and dissolving the mixture in 6 parts of acetone. The polyethylene glycol and cetyl polyglycol ether are then added. The resultant solution is sprayed on the kaolin and the acetone evaporated in vacuo.

wettable powders:
70%:
 70 parts active compound
 5 parts sodium dibutylnaphthylsulfonate
 3 parts naphthalenesulfonic acid/phenolsulfonic acid/formaldehyde condensate (3:2:1)
 10 parts kaolin
 12 parts Champagne chalk
40%:
 40 parts active compound
 5 parts sodium lignin sulfonate
 1 part sodium dibutylnaphthalenesulfonic acid
 54 parts silicic acid
25%:
 25 parts active compound
 4.5 parts calcium lignin sulfate
 1.9 parts Champagne chalk/hydroxyethyl cellulose (1:1)
 1.5 parts sodium dibutylnaphthalenesulfonate
 19.5 parts silicic acid
 19.5 parts Champagne chalk
 28.1 parts kaolin
25%:
 25 parts active compound
 2.5 parts isooctylphenoxy-polyethylene-ethanol
 1.7 parts Champagne chalk/hydroxyethyl cellulose (1:1)
 8.3 parts sodium aluminum silicate
 16.5 parts kieselguhr
 46 parts kaolin
10%:
 10 parts active compound
 3 parts of a mixture of sodium salts of saturated fatty alcohol sulfates
 5 parts naphthalenesulfonic acid/formaldehyde condensate
 82 parts kaolin These wettable powders are prepared by intimately mixing the active compounds with the additives in suitable mixers, and grinding the resulting mixtures in mills or rollers.

25% emulsifiable concentrate:
 25 parts active substance
 2.5 parts epoxidized vegetable oil
 10 parts of an alkylarylsulfonate/fatty alcohol polyglycol ether mixture 5 parts dimethylformamide
7.5 parts xylene

What is claimed is:

1. A compound having the formula

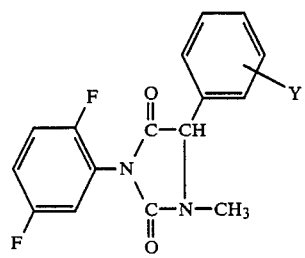

in which Y is a member selected from the group consisting of H, 2-F, 4-F, 3-Cl, 4-Cl, 2,4-di-Cl, 3,4-di-Cl, 2-Br, 3-Br, 4-Br, 4-I, 4-CH$_3$, 4-t-C$_4$H$_9$, 3-OCH$_3$, 4-OC$_2$H$_5$ and 3-OC$_6$H$_5$.

2. A compound according to claim 1 in which Y is a member selected from the group consisting of H, 2-F, 4-F, 3-Cl, 4-Cl, 3,4-di-Cl, 3-Br, 4-Br, 4-I, 4-CH$_3$, and 3-OCH$_3$.

3. A compound having the formula

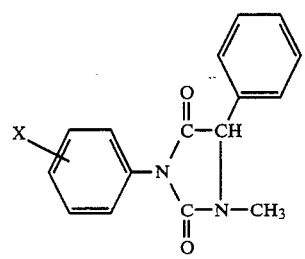

in which X is a member selected from the group consisting of 2-F, 3-Cl, 2,5-di-F-4-CH$_3$ and 2-F-5-OCH$_3$.

4. A compound according to claim 3 in which X is a member selected from the group consisting of 2-F and 3-Cl.

5. A compound having the formula

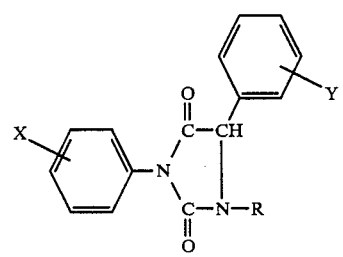

in which the combination of X, Y and R is a member selected from the group consisting of X=2,5-di-F, Y=H, and R=C$_2$H$_5$; X=2,5-di-F, Y=4-Br, and R=C$_2$H$_5$; X=3-CF$_3$, Y=H, and R=C$_2$H$_5$; X=3,4-di-Cl, Y=H, and R=C$_2$H$_5$; X=2,5-di-F, Y=H, and R=n-C$_4$H$_9$.

6. A compound according to claim 5 in which the combination of X, Y and R is a member selected from the group consisting of X=2,5-di-F, Y=H, and R=C$_2$H$_5$; and X=2,5-di-F, Y=4-Br, and R=C$_2$H$_5$.

7. An herbicidal composition comprising:
(a) an herbicidally effective amount of a compound having the formula

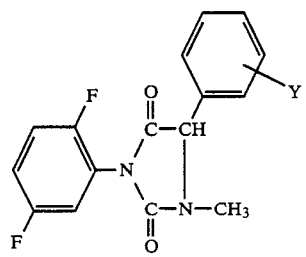

in which Y is a member selected from the group consisting of H, 2-F, 4-F, 3-Cl, 4-Cl, 2,4-di-Cl, 3,4-di-Cl, 2-Br, 3-Br, 4-Br, 4-I, 4-CH$_3$, 4-t-C$_4$H$_9$, 3-OCH$_3$, 4-OC$_2$H$_5$ and 3-OC$_6$H$_5$; and
(b) an herbicidally suitable inert diluent or carrier.

8. An herbicidal composition according to claim 7 in which Y is a member selected from the group consisting of H, 2-F, 4-F, 3-Cl, 4-Cl, 3,4-di-Cl, 3-Br, 4-Br, 4-I, 4-CH$_3$, and 3-OCH$_3$.

9. An herbicidal composition comprising:
(a) an herbicidally effective amount of a compound having the formula

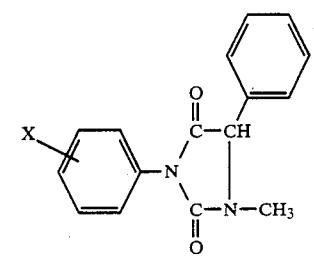

in which X is a member selected from the group consisting of 2-F, 3-Cl, 2,5-di-F-4-CH$_3$ and 2-F-5-OCH$_3$; and
(b) an herbicidally suitable inert diluent or carrier.

10. An herbicidal composition according to claim 9 in which X is a member selected from the group consisting of 2-F and 3-Cl.

11. An herbicidal composition comprising:
(a) an herbicidally effective amount of a compound having the formula

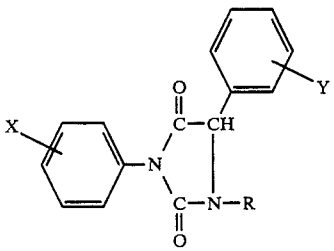

in which the combination of X, Y and R is a member selected from the group consisting of X=2,5-di-F, Y=H, and R=C$_2$H$_5$; X=2,5-di-F, Y=4-Br, and R=C$_2$H$_5$; X=3-CF$_3$, Y=H, and R=C$_2$H$_5$; X=3,4-di-Cl, Y=H, and R=C$_2$H$_5$; X=2,5-di-F, Y=H, and R=n-C$_4$H$_9$; and
(b) an herbicidally suitable inert diluent or carrier.

12. An herbicidal composition according to claim 11 in which the combination of X, Y and R is a member selected from the group consisting of X=2,5-di-F, Y=H, and R=$C_2H_5$; and X=2,5-di-F, Y=4-Br, and R=$C_2H_5$.

13. A method of controlling undesirable vegetation comprising applying to said vegetation or to the locus thereof an herbicidally effective amount of a compound having the formula

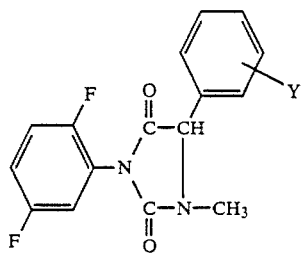

in which Y is a member selected from the group consisting of H, 2-F, 4-F, 3-Cl, 4-Cl, 2,4-di-Cl, 3,4-di-Cl, 2-Br, 3-Br, 4-Br, 4-I, 4-$CH_3$, 4-t-$C_4H_9$, 3-$OCH_3$, 4-$OC_2H_5$ and 3-$OC_6H_5$.

14. A method according to claim 13 in which Y is a member selected from the group consisting of H, 2-F, 4-F, 3-Cl, 4-Cl, 3,4-di-Cl, 3-Br, 4-Br, 4-I, 4-$CH_3$, and 3-$OCH_3$.

15. A method of controlling undesirable vegetation comprising applying to said vegetation or to the locus thereof an herbicidally effective amount of a compound having the formula

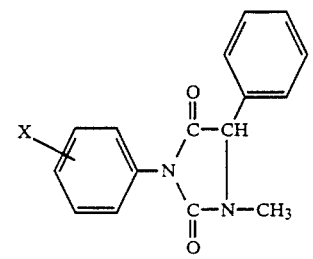

in which X is a member selected from the group consisting of 2-F, 3-Cl, 2,5-di-F-4-$CH_3$ and 2-F-5-$OCH_3$.

16. A method according to claim 15 in which X is a member selected from the group consisting of 2-F and 3-Cl.

17. A method of controlling undesirable vegetation comprising applying to said vegetation or to the locus thereof an herbicidally effective amount of a compound having the formula

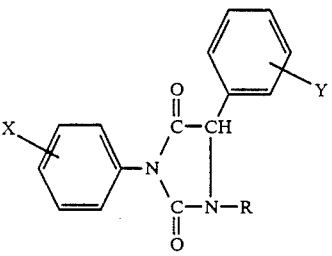

in which the combination of X, Y and R is a member selected from the group consisting of X=2,5-di-F, Y=H, and R=$C_2H_5$; X=2,5-di-F, Y=4-Br, and R=$C_2H_5$; X=3-$CF_3$, Y=H, and R=$C_2H_5$; X=3,4-di-Cl, Y=H, and R=$C_2H_5$; X=2,5-di-F, Y=H, and R=n-$C_4H_9$.

18. A method according to claim 17 in which the combination of X, Y and R is a member selected from the group consisting of X=2,5-di-F, Y=H, and R=$C_2H_5$; and X=2,5-di-F, Y=4-Br, and R=$C_2H_5$.

* * * * *